United States Patent [19]

Izawa et al.

[11] Patent Number: 4,997,923

[45] Date of Patent: Mar. 5, 1991

[54] DIHYDRATE CRYSTALS OF ETOPOSIDE-2-DIMETHYLAMINO COMPOUND HYDROCHLORIDE AND A PROCESS FOR PRODUCTION THEREOF

[75] Inventors: Takao Izawa, Koga; Tadashi Fujii, Iwatsuki; Yukio Chikui; Kazuo Ohtsuki, both of Tokyo, all of Japan

[73] Assignee: Nippon Kayaku Kabushiki Kaisha, Tokyo, Japan

[21] Appl. No.: 434,777

[22] Filed: Nov. 13, 1989

[30] Foreign Application Priority Data

Nov. 16, 1988 [JP] Japan ................................ 63-287811
Nov. 16, 1988 [JP] Japan ................................ 63-287812

[51] Int. Cl.$^5$ .......................... C07H 1/06; C07H 5/06; C07H 15/26
[52] U.S. Cl. .................................. 536/17.2; 536/4.1; 536/18.1; 536/127
[58] Field of Search ...................... 536/4.1, 17.2, 18.1, 536/127

[56] References Cited

FOREIGN PATENT DOCUMENTS 0196618 10/1986 European Pat. Off. .

OTHER PUBLICATIONS

Chemical Pharmaceutical Bulletin, vol. 34, No. 9, Sep. 9, 1986, pp. 3741–3746.
Chemistry Letters, No. 5, May 5, 1987, pp. 799–802.

Primary Examiner—Ronald W. Griffin
Assistant Examiner—Nancy S. Carson
Attorney, Agent, or Firm—Henry C. Nields

[57] ABSTRACT

The present invention provides novel dihydrate crystals of etoposide-2-dimethylamino compound hydrochloride [4'-demethylepipodophillotoxin 9-(4,6-O-ethylidene-2-dimethylamino-2-deoxy-$\beta$-D-glucopyranoside hydrochloride] used as a carcinostatic agent and a process for production thereof.

3 Claims, 3 Drawing Sheets

DIHYDRATE CRYSTALS OF ETOPOSIDE-2-DIMETHYLAMINO COMPOUND HYDROCHLORIDE AND A PROCESS FOR PRODUCTION THEREOF

BACKGROUND OF THE INVENTION

1. Field of the Invention

The present invention relates to dihydrate crystals of 4'-demethylepipodophyllotoxin 9-(4,6-O-ethylidene-2-dimethylamino-2-deoxy-β-D-glucopyranoside (hereinafter referred to as etoposide-2-dimethylamino compound) hydrochloride having a potent carcinostatic activity. The present invention also relates to a process for production of etoposide-2-dimethylamino compound hydrochloride dihydrate crystals.

2. Description of the Prior Art

Etoposide-2-dimethylamino compound and its hydrochloride are disclosed in EP-A-0196618 [Japanese Patent Application KOKAI (Laid-open) No. 61-227590]. The compound has a potent carcinostatic activity and is expected to be effective as a carcinostatic agent.

However, the etoposide-2-dimethylamino compound and its hydrochloride are hygroscopic. In the case of the hydrochloride, there is a shortcoming that organic solvents such as acetone, methanol or the like which are used to form the hydrochloride remain (0.3 to 5%) in the crystals.

The remaining organic solvents become a problem when the etoposide-2-dimethylamino compound is used as a drug. The hygroscopic property also becomes a problem in designing medical preparations.

SUMMARY OF THE INVENTION

As a result of extensive investigations on the etoposide-2-dimethylamino compound having neither organic solvent contaminants nor hygroscopic property which is suited for medical preparations, the present inventors have accomplished the present invention.

Therefore, an object of the present invention is to provide novel dihydrate crystals of the etoposide-2-dimethylamino compound hydrochloride which contain no organic solvents are not hygroscopic and are suitable for medical preparations.

Another object of the present invention is to provide a novel process for producing the etoposide-2-dimethylamino compound or its salt.

DESCRIPTION OF THE PREFERRED EMBODIMENTS

Figure 1:
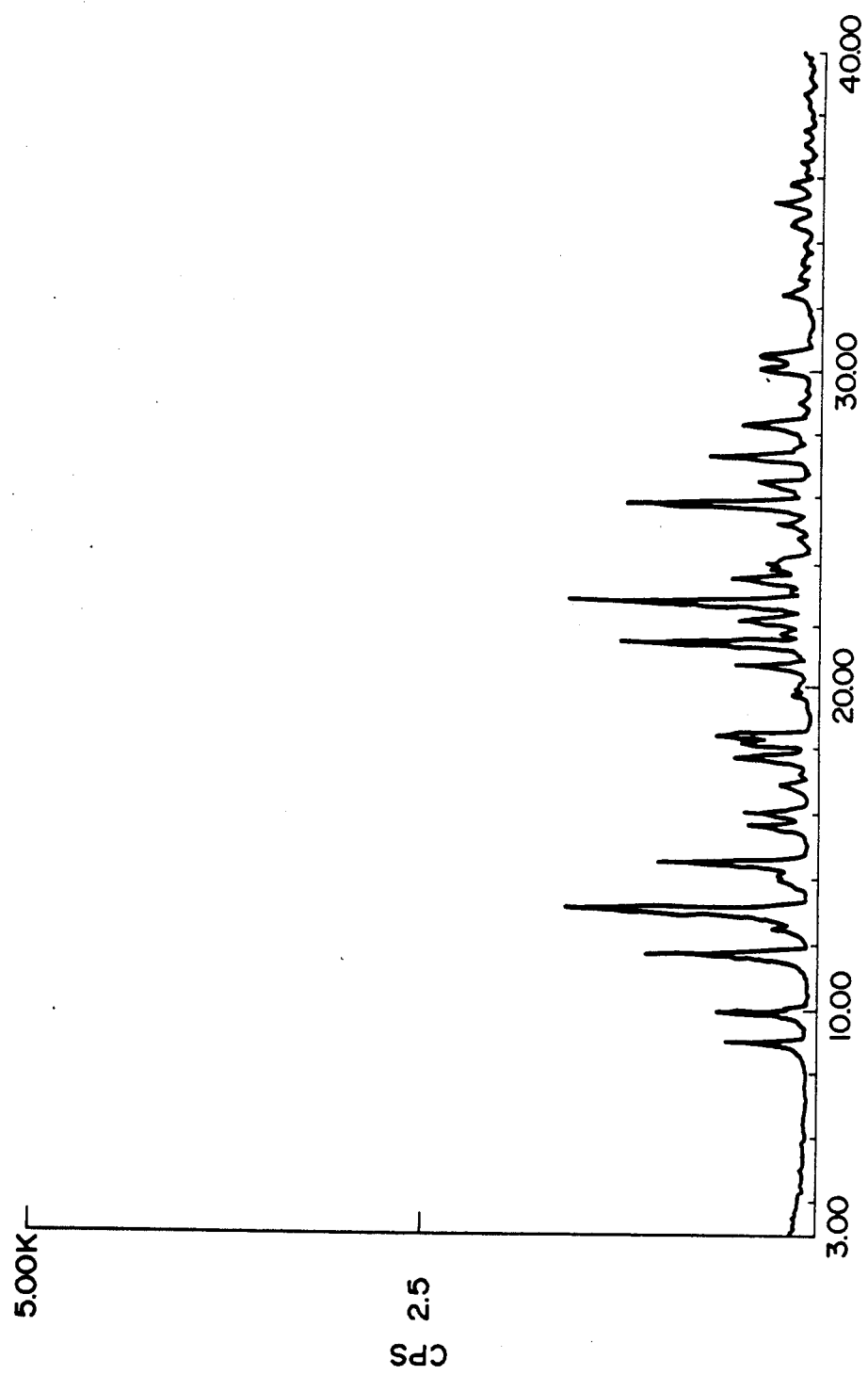
FIG. 1 shows an X ray diffraction pattern of etoposide-2-dimethylamino compound hydrochloride dihydrate crystals of γ type.
Figure 2:
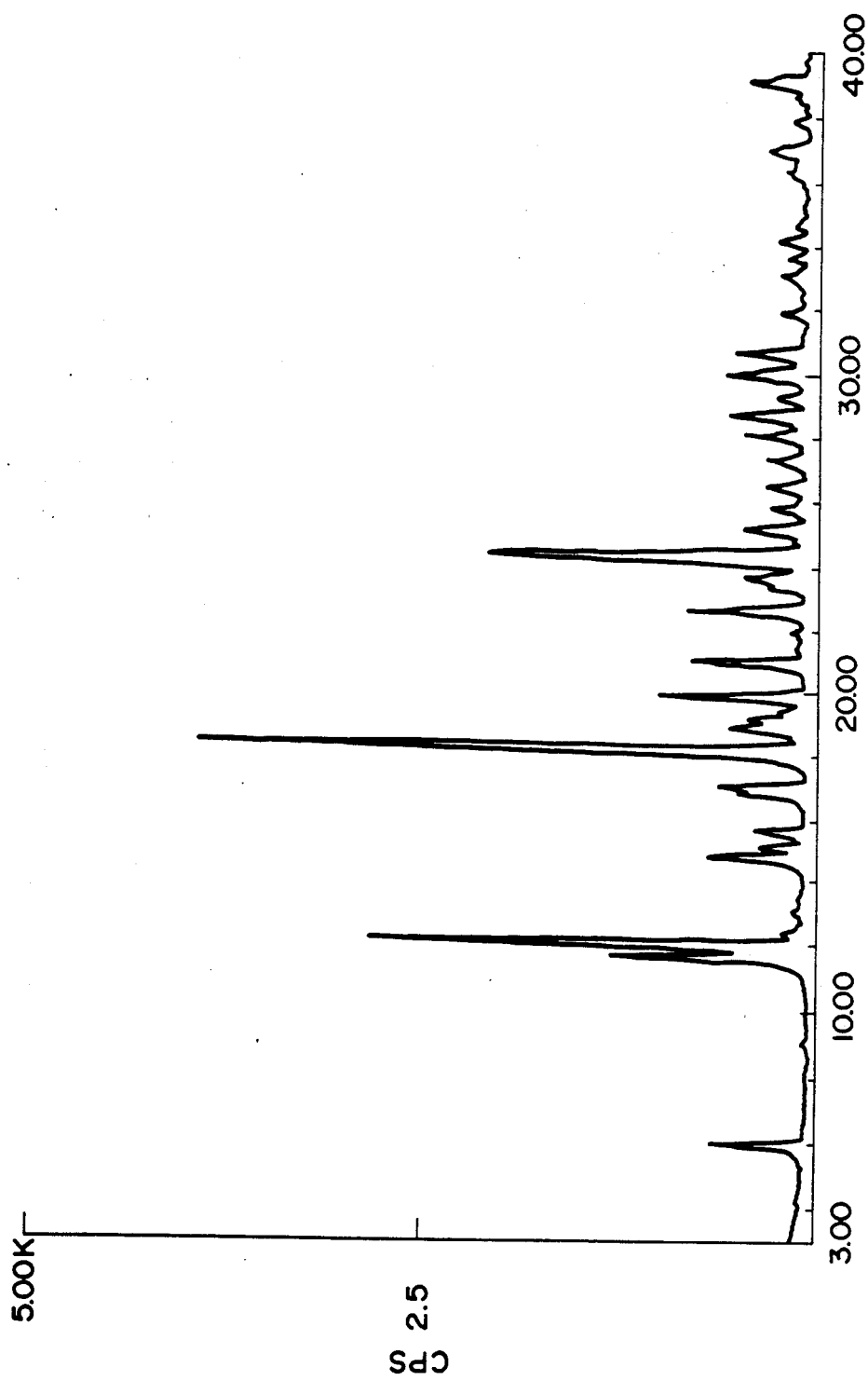
FIG. 2 shows an X ray diffraction pattern of etoposide-2-dimethylamino compound hydrochloride dihydrate crystals of β type.
Figure 3:
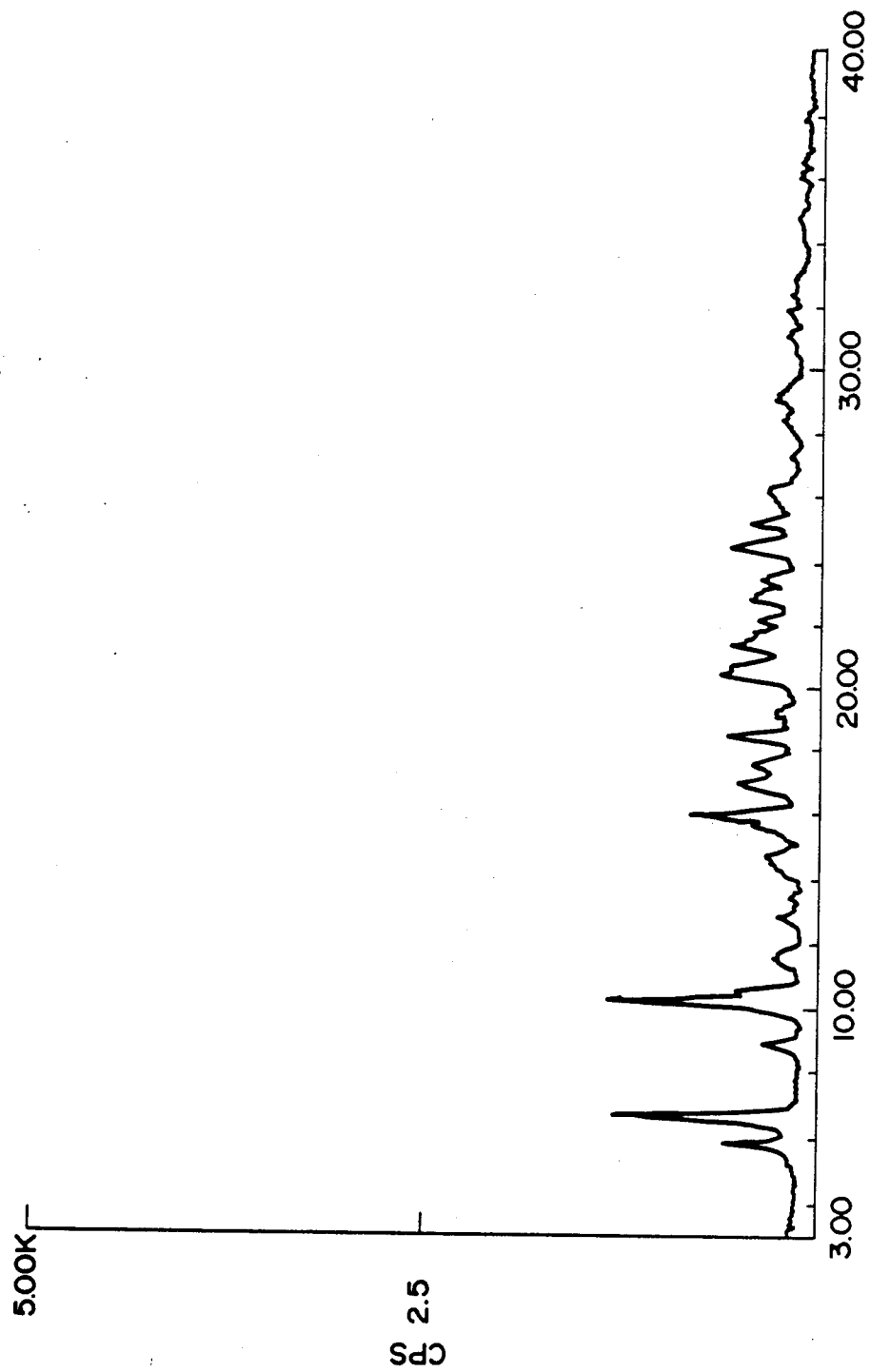
FIG. 3 shows an X ray diffraction pattern of anhydrous etoposide-2-dimethylamino compound hydrochloride.

[A] Production of etoposide-2-dimethylamino compound hydrochloride dihydrate crystals The etoposide-2-dimethylamino compound hydrochloride dihydrate crystals of the present invention can be produced as follows.

That is, the present inventors have found that by suspending in water the substantially anhydrous etoposide-2-dimethylamino compound containing organic solvents and converting the same into crystals of etoposide-2-dimethylamino compound hydrochloride dihydrate represented by the following formula: [I]

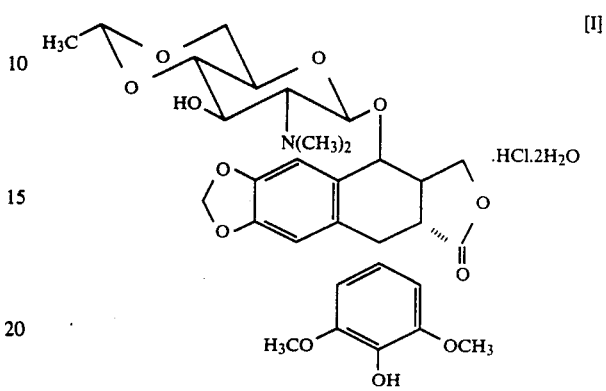

crystals of high purity which are substantially free of organic solvents can be obtained and, have attained the present invention.

The present invention is described below in more detail. In general, the etoposide-2-dimethylamino compound hydrochloride can be obtained as crystals by dissolving the free etoposide-2-dimethylamino compound in organic solvents such as acetone, methanol or the like and blowing hydrogen chloride gas into the solution. The hydrochloride contains, even after drying, the organic solvents such as acetone or methanol used to form the hydrochloride. The organic solvents cannot be removed by any ordinary method for drying, for example, elevating a drying temperature, prolonging a drying time, grinding the crystals into powders and drying the powders again, etc. In addition, it is difficult to accurately determine the content of the etoposide-2-dimethylamino compound because the hydrochloride is hygroscopic. These are problems as starting material for medical preparation. According to the process of the present invention, the crystals containing organic solvent such as acetone, methanol, etc. are suspended in at least approximately 2-fold amount (V/W), preferably approximately 3 to 30-fold amount (V/W), more preferably approximately 5 to 10-fold amount (V/W) of water at temperature of approximately 0° to 40° C., preferably approximately 5° to 35° C. over at least several minutes, preferably about 0.2 to about a few hour, more preferably about 0.3 to about 1.6 hour.

By this treatment, one type of the hydrochloride dihydrate crystals (β type crystals) are formed. The crystals are filtered with slightly difficulty. Therefore, if necessary and desired, the crystals may be subjected to the following treatment to form another type of the hydrochloride dihydrate crystals (γ type crystals). That is, the β type crystals can be converted into the etoposide-2-dimethylamino compound hydrochloride dihydrate γ type crystals capable of being readily filtered by stirring the suspension of the β type crystals with heating at a temperature higher than 20° C., preferably at about 30° to about 80° C., more preferably about 40° to about 60° C. for about 0.5 to about 5 hours, preferably about 1 to about 2 hours, cooling the suspension again to about 5° to about 10° C., then filtering the crystals and drying the crystals in vacuum (25° to 30° C., 5 hours).

In the conventional technique, the organic solvents used at the final step remain in the crystals in considerable amounts; even though drying conditions are varied, the residual organic solvents cannot be removed (Table 1) and the resulting crystals tend to be hygroscopic in the air (Table 2). Accordingly, the crystals obtained by the prior art process are not suited for medical preparations. According to the present invention, however, the etoposide-2-dimethylamino compound hydrochloride containing organic solvents can be easily converted into the dihydrate crystals by suspending the hydrochloride in water. The resulting dihydrate crystals are best suited for medical preparations since the dihydrate crystals are free of hygroscopic nature and have a minimized content of the residual solvents.

TABLE 1

Residual Solvent in the Crystals

| No. | Final Solvent Used | Drying Conditions (°C./mmHg/hr) | Amount of Residual Solvent (ppm)/Residual Solvent | Note |
|---|---|---|---|---|
| 1 | Methanol* | 50/2/7 | 54,000/methanol | |
| 2 | " | 75/2/7 | 52,800/methanol | No. 1 was again dried at high temperature. |
| 3 | Acetone | 65/2/5 | 2,800/acetone | |
| 4 | " | 75/2/7 | 2,800/acetone | No. 3 was again dried at high temperature. |
| 5 | " | 75/2/5 | 2,750/acetone | No. 4 was ground into powders and again dried. |

*Free etoposide-2-dimethylamino compound was dissolved in methanol, hydrogen chloride gas was blown into the solution and the precipitated crystals were separated and dried.

TABLE 2

Results on Moisture Test

Weight increase (%) when stored in the atmosphere under relative humidity of 93% at 25° C.

| Time (hour) | 0 | 5 | 10 | 30 | 85 |
|---|---|---|---|---|---|
| Control* | 0 | 1.6 | 2.8 | 2.9 | 2.9 |
| Crystals of invention (β type crystals and γ type crystals) | 0 | 0 | 0 | 0 | 0 |

*No. 13 crystals shown in Table 1 were used.

PRODUCTION EXAMPLE OF THE β TYPE CRYSTALS AND THE γ TYPE CRYSTALS

Example

After 20.0 g of etoposide-2-dimethylamino compound hydrochloride crystals* (containing about 5000 ppm of acetone) and 100 ml of distilled water were charged in a four-necked flask of 200 ml, the mixture was stirred for an hour at an inner temperature of 5° C. to form the etoposide-2-dimethylamino compound hydrochloride dihydrate crystals (β type crystals). Thereafter the inner temperature was raised to 60° C. After stirring for an hour, the mixture was again cooled to 10° C. The crystals were filtered by suction and then dried in vacuum (30° C./2 mmHg/5 hours) to give 19.7 g (yield: 93.5%) of the etoposide-2-dimethylamino compound hydrochloride dihydrate crystals (γ type crystals). Analysis of the thus obtained β type crystals and γ type crystals by gas chromatography revealed that the residual acetone was 27 ppm and 25 ppm, respectively.

*Free etoposide-2-dimethylamino compound was dissolved in acetone, hydrogen chloride gas was blown into the solution and the precipitated hydrochloride crystals were separated and dried.

β type crystals:
Melting point: 194° C. (decomposed)
Optical rotation: $[\alpha]_D^{20} - 90.3°$ [C=0.5 (When calculated as dehydrated product), methanol]
IR: 3420, 3350, 3270, 3000, 2950, 2900, 1775, 1110 (cm$^{-1}$)
Moisture content: 5.70%
NMR: identical with those of the product separately synthesized.

γ type crystals:
Melting point: 217°-220° C. (decomposed)
Optical rotation: $[\alpha]_D^{20} - 90°$ [C=0.5 (When calculated as dehydrated product), ethanol]
IR: 3650, 3550, 3430, 3200, 1775, 1110 (cm$^{-1}$)
Moisture content: 5.30%
NMR: identical with those of the product separately synthesized.

[B] Production of the etoposide-2-dimethylamino compound as the starting material and its salt The present inventors have also made investigations on a process for producing the etoposide-2-dimethylamino compound used in the present invention.

For the production of the etoposide-2-dimethylamino compound, there is known a method which comprises reacting 4'-demethylepipodophyllotoxin-β-D-2-amino-2-deoxy-4,6-O-ethylidene-glucopyranoside (hereinafter referred to as etoposide-2-amino compound) represented by formula [II]:

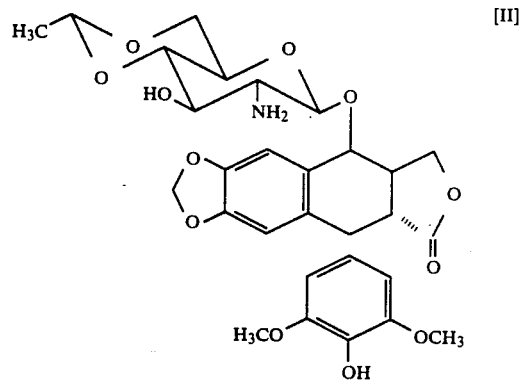

with an aldehyde represented by formula [III]:

HCHO           [III]

and sodium borohydride cyanide in an inert solvent (EP-A-0 196 618)[Japanese Patent Application KOKAI (Laid-open) No. 61-227590].

However, the method involves defects that (1) amounts of by-products increase unless sodium borohydride cyanide is added in a short period of time; (2) increase in production scale results in vigorous generation of heat and foam so that it is difficult to add sodium borohydride cyanide in a short period of time; (3) since sodium borohydride cyanide is strongly alkaline, it tends to form decomposition products so that it is necessary to adjust pH of the reaction solution and an acid is previously incorporated; in that case, decomposition products are formed because of the acid, with reduced yield as expected; (4) since there is a fear that sodium borohydride cyanide might generate very noxious hydrogen cyanide, there are problems of industrial hygiene in industrial production and, if possible, it is desired to avoid its use; (5) sodium borohydride cyanide is available as a reagent grade but it is impossible to get the reagent grade in the amounts required for an industrial scale, etc. Therefore, the method is problematic from industrial viewpoints.

Therefore, the present inventors have made extensive investigations on a process for industrial production of the etoposide-2-dimethylamino compound hydrochloride dihydrate crystals shown by formula below or its salt which raises no problem in industrial hygiene, has no restriction to raw materials and can be produced in high quality and high yield. As a result, they have found that the following process is suited for the industrial production.

That is, the etoposide-2-dimethylamino compound represented by formula [I']:

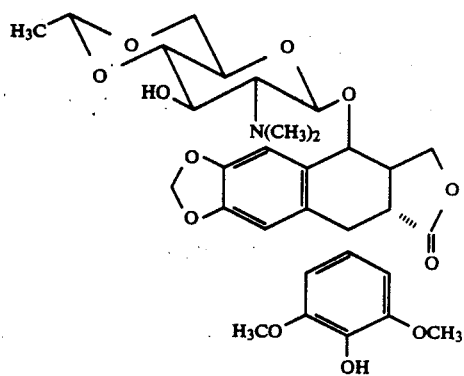

can be obtained in good yield, by reacting the etoposide-2-amino compound represented by formula [II] given above with an aldehyde represented by formula [III]:

HCHO                                               [III]

and then hydrogenating the resulting product in the presence of a metal catalyst.

The above-mentioned process is greatly advantageous in that the compound of formula [I'] can be quantitatively produced and hence, the desired product can be obtained in high purity and high yield only by removing the catalyst from the reaction solution and then concentrating to dryness.

The process is described in more detail: the compound shown by formula [II] which is used as the starting material is known (Japanese Patent Application KOKAI No. 60-32799). The aldehyde shown by formula [III] is formaldehyde. Alternatively, compounds that release formaldehyde in the reaction may also be used as the aldehyde.

The reaction of the compound of formula [II] with the aldehyde of formula [III] is carried out generally at room temperature. It is also possible to conduct the reaction at the same time as the reduction proceeds. In this case, the reaction is carried out at the temperature for the reduction.

It may be sufficient to use the aldehyde of formula [III] in at least 2 molar amounts, preferably 2 to 4 molar amounts, based on the compound of formula [II]. Any metal catalyst is usable so long as it is generally used for reduction. Examples of the catalyst include noble metal catalysts (platinum, palladium, rhodium, etc. and Raney nickel, etc.), among which palladium is preferable. Any of palladium black and palladium carbon can be used as palladium catalyst. It is sufficient to use, for example, about 1 to about 50%, generally about 5 to about 20% of palladium calculated as metal based on the compound of formula [II]. The reduction may be carried out in an autoclave at about 0° to about 150° C., generally about 5° to about 100° C., preferably about 40° to about 60° C. A theoretical amount of hydrogen necessary for the reaction is required as hydrogen. The reaction can be carried out under normal pressure, preferably under pressure. The initial pressure is generally set in the range of from about 1 kg/cm² (gauge pressure, hereafter the same) to about 20 kg/cm², preferably about 5 to about 10 kg/cm². As the reaction proceeds, hydrogen may be supplemented.

Any solvent is usable as the solvent for the reaction as long as it can dissolve the starting etoposide-2-amino compound of formula [II] or its salt. The solvent may be any of polar solvents and non-polar solvents. Specific examples of the solvent include alcohols such as methanol, ethanol, propanol, etc.; halogenated hydrocarbons such as chloroform, methylene chloride, 1,2-dichloroethane, etc.; acetonitrile, acetic acid, water, and the like.

The compound of formula [II] used in the reaction may be salts with inorganic acids or organic acids. Specific examples of the acid include inorganic acids such as hydrochloric acid, sulfuric acid, phosphoric acid, etc. and organic acids such as acetic acid, formic acid, oxalic acid, etc.

According to the present reaction, no by-product is produced but Schiff's base is formed as the intermediate. The intermediate can be quantitatively converted into the compound of formula [I']. Thus, only the compound of formula [I'] is contained in the reaction solution after the reaction is completed.

Therefore, it is extremely simple to isolate the crystals from the reaction solution. It is sufficient that after filtering the catalyst, the filtrate be merely concentrated to dryness. The etoposide-2-dimethylamino compound of formula [I'] or its salt can thus be obtained quantitatively in high purity.

The etoposide-2-dimethylamino compound shown by formula [I'] or its salt is a derivative of 4'-demethylepipodophyllotoxin-$\beta$-D-4,6-O-ethylideneglucopyranoside (general name: Etoposide) and is an expensive compound expected to be developed as a drug.

According to the process of the present invention, the use of any raw material which becomes problems in industrial hygiene can be avoided and complicated purification by silica gel chromatography or the like that has been heretofore required is unnecessary. In addition, the process can produce pure crystals of the etoposide-2-dimethylamino compound quantitatively, which leads to reduction in production costs. Therefore, the instant process is extremely effective as an industrial process.

Comparison between the process of the present invention and the prior art process [EP-A-0 196 618 (Japanese Patent Application KOKAI (Laid-open) No. 61-227590] is shown in Table 3:

TABLE 3

| Process | Product Compound [I'] | Kind of By-Product | Purification | Yield (%) |
|---|---|---|---|---|
| Invention (Example (a)) | 100% | none | unnecessary | 97.5 |
| Control (EP-A-0 196 618) | ca. 50% | 6-7 kinds | silica gel chromatography | 35.3 |

1 PRODUCTION EXAMPLE OF ETOPOSIDE-2-DIMETHYLAMINO COMPOUND

Example (a)

In 20 ml of methanol was suspended 2.0 g (3.4 mmols) of the etoposide-2-amino compound and, 1.2 g of 35% formalin aqueous solution was added to the suspension. After stirring at room temperature for about 30 minutes, 1.5 g of 10% palladium carbon was added to the reaction mixture followed by stirring in an autoclave at 50° C. under hydrogen pressure of 5 to 10 kg/cm².

Two hours after, the catalyst in the reaction solution was filtered off and the filtrate was concentrated under reduced pressure to give 2.0 g of the etoposide-2-dimethylamino compound as white crystals (yield, 97.5%).

The melting point, optical rotation, NMR and MS (Mass Spectrometry) of the resulting crystals were identical with those of the etoposide-2-dimethylamino compound obtained by the process disclosed in EP-A-0 196 618 (Japanese Patent Application KOKAI (Laid-open) No. 61-227590).

Example (b)

In 500 ml of acetonitrile was suspended 42.0 g (0.071 mmol) of the etoposide-2-amino compound and, 24.4 g of 35% formalin aqueous solution was added to the suspension. After stirring at room temperature for an hour, 10.0 g of palladium black was added to the reaction mixture.

The mixture was reacted in an autoclave at 55° C. for about 4 hours under hydrogen pressure of 8 to 10 kg/cm². The reaction mixture was treated in a manner similar to Example (a) to give 43.4 g of the etoposide-2-dimethylamino compound (yield, 99.2%). The melting point, optical rotation and NMR of the resulting crystals were identical with those of the crystals obtained in Example (a).

Example (c)

In a solvent mixture of 50 l of methanol and 50 l of methylene chloride was suspended 5.12 kg (7.91 mols) of the etoposide-2-amino compound acetate and, 680 g of 35% formalin aqueous solution was added to the suspension. After stirring at room temperature for 30 minutes, 3.9 kg of palladium carbon was added to the reaction mixture.

The mixture was reacted in an autoclave at 45° for about 3 hours under hydrogen pressure of 5 to 10 kg/cm². After cooling, the catalyst was filtered off and the filtrate was extracted with a sodium hydrogen-carbonate aqueous solution. After washing the organic layer was concentrated under reduced pressure to give 4.73 kg of the etoposide-2-dimethylamino compound as white crystals (yield, 97.1%).

The melting point, optical rotation and NMR of the resulting crystals were identical with those of the crystals obtained in Example (a).

Example (d)

In 100 ml of methanol was suspended 65 g of the etoposide-2-amino compound hydrochloride and, 50 g of 35% formalin aqueous solution was added to the suspension. After stirring at 40° C. of the liquid temperature for 30 minutes, 37 g of 10% palladium carbon and 60 ml of methanol were added to the mixture followed by reacting in an autoclave at about 45° C. for about 3 hours under hydrogen pressure of 5 to 10 kg/cm². After cooling, the catalyst was filtered off and the filtrate was concentrated under reduced pressure. The precipitated crystals were filtered to give the etoposide-2-dimethylamino compound hydrochloride.

REFERENCE EXAMPLE

Production of the etoposide-2-dimethylamino compound by known process:

In 3.5 l of methanol was suspended 338 g (0.576 mol) of the etoposide-2-amino compound and, 200 ml of 35% formalin aqueous solution and 30 ml of acetic acid were added to the suspension. After stirring at room temperature for 30 minutes, a solution of 36 g (0.576 mol) of sodium borohydride cyanaide in 350 ml of methanol was dropwise added to the mixture. After completion of the reaction, chloroform, water and sodium carbonate were added to the reaction mixture to perform extraction. After further washing the extract with water, the organic layer was concentrated under reduced pressure to give the residue. The resulting residue was crystallized from methanol and the crystals were purified by silica gel chromatography to give 124.6 g (yield, 35.3%) of 4'-demethylepipodophyllotoxinetoposide-2-dimethylamino compound.

[C] Production of the etoposide-2-dimethylamino compound hydrochloride:

Free etoposide-2-dimethylamino compound is dissolved in an organic solvent such as methanol, acetone or the like. After cooling to, preferably about 0° to about 10° C., hydrogen chloride is added to the solution. It is preferred that hydrogen chloride be added generally in the form of a solution of hydrogen chloride in an organic solvent, for example, a methanolic solution, etc. Alternatively, hydrogen chloride may also be blown into the system in a gaseous state.

The mixture is reacted for about 0.5 to about 2 hours with stirring. The precipitated crystals are filtered to give the etoposide-2-dimethylamino compound hydrochloride.

In the case that the hydrochloride is obtained in step [B] described above, the hydrochloride may be generally used as it is; if necessary and desired, the hydrochloride may be once converted into the free state with an alkali and the free compound may be again rendered the hydrochloride with hydrogen chloride. [Production Example of the etoposide-2-dimethylamino compound hydrochloride]

Free etoposide-2-dimethylamino compound 7 g, is dissolved in 160 ml of acetone. After cooling to below about 5° C. of the liquid temperature, a solution of about 0.4 g of hydrogen chloride in 20 ml of methanol was added to the mixture followed by stirring for an hour. The precipitated crystals are filtered and dried in vacuum to give anhydrous etoposide-2-dimethylamino compound hydrochloride as crystals.

What is claimed is:

1. Crystals of 4'-demethylepipodophyllotoxin-9(4,6-O-ethylidene-2-dimethylamino-2-deoxy-β-D- glucopyranoside hydrochloride dihydrate represented by formula:

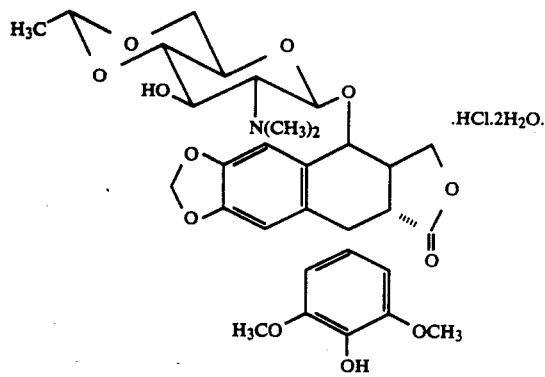

2. A process for producing the crystals of claim 1 which comprises suspending the 4'-demethylepipodophyllotoxin 9-(4,6-O-ethylidene-2-dimethylamino-2-deoxy-β-D-glucopyranoside hydrochloride in water.

3. A process for producing etoposide-2-dimethylamino compound hydrochloride dihydrate crystals which comprises reacting 4'-demethylepipodophyllotoxin-β-D-2-amino-2-deoxy-4,6-O-ethylidene-glucopyranoside represented by formula [II]:

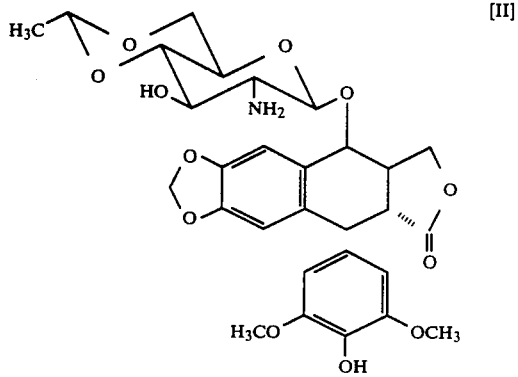

or a salt thereof with an aldehyde represented by formula [III]:

HCHO  [III]

and then hydrogenating the resulting product in the presence of a metal catalyst to give the etoposide-2-dimethylamino compound or a salt thereof;
(a) converting the resulting etoposide-2-dimethylamino compound into the hydrochloride in an organic solvent, after making the salt free in the case that the resulting etoposide-2-dimethylamino compound is a salt other than the hydrochloride, and in the case that the etoposide-2-dimethylamino compound is in the free state as it is;
(b) further in the case that the resulting etoposide-2-dimethylamino compound is the hydrochloride, suspending the hydrochloride in water.

* * * * *